(12) United States Patent
Qi et al.

(10) Patent No.: US 10,933,162 B2
(45) Date of Patent: Mar. 2, 2021

(54) IMPLANTABLE MEDICAL INSTRUMENT PREFORM, IMPLANTABLE MEDICAL INSTRUMENT AND PREPARATION METHOD THEREOF

(71) Applicant: Lifetech Scientific (Shenzhen) Co., Ltd., Shenzhen (CN)

(72) Inventors: Zuqiang Qi, Shenzhen (CN); Xiaole Jia, Shenzhen (CN); Zhou Chen, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 0 days.

(21) Appl. No.: 15/575,928

(22) PCT Filed: May 17, 2016

(86) PCT No.: PCT/CN2016/082311
§ 371 (c)(1),
(2) Date: Nov. 21, 2017

(87) PCT Pub. No.: WO2016/188342
PCT Pub. Date: Dec. 1, 2016

(65) Prior Publication Data
US 2018/0147322 A1 May 31, 2018

(30) Foreign Application Priority Data
May 22, 2015 (CN) .......................... 201510268908.5

(51) Int. Cl.
*A61L 27/34* (2006.01)
*A61L 27/04* (2006.01)
(Continued)

(52) U.S. Cl.
CPC ................ *A61L 27/34* (2013.01); *A61F 2/06* (2013.01); *A61L 27/04* (2013.01); *A61L 27/30* (2013.01);
(Continued)

(58) Field of Classification Search
CPC .... A61L 2420/02; A61L 27/34; A61L 31/084; A61L 33/068; A61L 31/14; A61L 31/10;
(Continued)

(56) References Cited

U.S. PATENT DOCUMENTS

2006/0251795 A1* 11/2006 Kobrin .................... A61L 27/34
427/2.1
2007/0281117 A1* 12/2007 Kaplan ..................... A61F 2/91
428/35.7
(Continued)

FOREIGN PATENT DOCUMENTS

CN 1618472 5/2005
CN 1618472 A * 5/2005
(Continued)

OTHER PUBLICATIONS

CN1618472A_translation (Year: 2005).*
(Continued)

*Primary Examiner* — Brian A Dukert
*Assistant Examiner* — Rebecca Lynee Zimmerman
(74) *Attorney, Agent, or Firm* — Raymond Sun

(57) ABSTRACT

Disclosed are an implantable medical device, a preparation method thereof and an implantable medical device preform for the preparation of the implantable medical device. The implantable medical device comprises a metal basal body (21) and a polymer film layer (22) covering the surface of the metal basal body (21) and preventing endothelium growth and covering, and also comprises a transitional body (23), which is located between the metal basal body (21) and
(Continued)

the polymer film layer (22) and covers at least part of the surface of the metal basal body (21), wherein the transitional body (23) is connected to the polymer film layer (22) and the metal basal body (21). By arranging the transitional body (23) to be connected to the polymer film layer (22) and the metal basal body (21), the polymer film layer (22) will not easily fall off when being implanted into a human body.

9 Claims, 4 Drawing Sheets

(51) Int. Cl.
| | |
|---|---|
| *A61L 27/30* | (2006.01) |
| *A61L 27/50* | (2006.01) |
| *A61L 31/14* | (2006.01) |
| *A61L 33/06* | (2006.01) |
| *A61L 31/10* | (2006.01) |
| *A61L 31/08* | (2006.01) |
| *A61F 2/06* | (2013.01) |
| *A61L 27/42* | (2006.01) |
| *A61M 31/00* | (2006.01) |

(52) U.S. Cl.
CPC .............. *A61L 27/50* (2013.01); *A61L 31/084* (2013.01); *A61L 31/088* (2013.01); *A61L 31/10* (2013.01); *A61L 31/14* (2013.01); *A61L 33/068* (2013.01); *A61L 27/422* (2013.01); *A61L 2400/10* (2013.01); *A61L 2420/02* (2013.01); *A61L 2420/08* (2013.01); *A61M 31/002* (2013.01)

(58) Field of Classification Search
CPC ........ A61L 31/088; A61L 27/04; A61L 27/50; A61L 27/30; A61L 2420/08; A61L 2400/10; A61L 27/422; A61F 2/06; C23C 16/26; B51J 2/1642; A61M 31/002; B51L 2/1642
See application file for complete search history.

(56) References Cited

U.S. PATENT DOCUMENTS

| | | | |
|---|---|---|---|
| 2009/0005862 A1* | 1/2009 | Nakatani | A61F 2/91 623/1.49 |
| 2015/0099123 A1* | 4/2015 | Barbee | C23C 16/26 428/408 |

FOREIGN PATENT DOCUMENTS

| | | |
|---|---|---|
| CN | 101147705 | 3/2008 |
| CN | 102330059 | 1/2012 |
| WO | WO2009086205 | 7/2009 |

OTHER PUBLICATIONS

Furlan et al "Diamond-like carbon films deposited by hydrocarbon plasma sources" (2013) Reviews on Advanced Materials Science, Dec. 2013) (Year: 2013).*

Johnston, E., et al "Plasma Deposition and Surface Characterization of Oligoglyme, Dioxane, and Crown Ether Nonfouling Films", Langmuir (2005), 21, 870-881. (Year: 2005).*

PCT International Search Report for WO2016/188342.

* cited by examiner

IMPLANTABLE MEDICAL INSTRUMENT PREFORM, IMPLANTABLE MEDICAL INSTRUMENT AND PREPARATION METHOD THEREOF

TECHNICAL FIELD

The present invention relates to the field of medical devices, and in particular, to an implantable medical device preform, implantable medical device and preparation method thereof.

BACKGROUND OF THE INVENTION

Pulmonary embolism (PE) is a common disease with a high case-fatality rate. Statistical data shows that the mortality of untreated pulmonary embolism is 20%-30%; new cases per year account for about 0.2% of the total population, and if calculation is made based on China's 1.35 billion people, there are about 2.7 million new patients suffering from pulmonary embolism every year. It is clinically proven that vena cava filters (hereinafter referred to as filters) are able to reduce the incidence of pulmonary embolism. Filters are generally made of metal, which are divided into permanent implantable filters and temporary filters. In either case, after filters are implanted into the vena cava for a period of time, due to their contact with blood and vascular endothelium, endothelium growth and covering such as protein absorption and platelet adhesion may occur, and eventually, thrombi are formed. As a result, vein blood vessels are blocked, or pulmonary embolism reoccurs. Particularly, for temporary filters, the above endothelium growth and covering may also injure endangium when the filters are removed, thus posing a greater challenge to the removal of the filters.

The surface of the metal basal body of a filter is attached thereon with a polymer film layer preventing endothelium growth and covering, such as a polyethylene glycol-like (PEG-like) thin film. The polymer film layer generally has a thickness of less than 3 μm, which can improve bioadhesion resistant properties of the surface of the filter, inhibit the interaction of the surface of the filter with inner walls of blood vessels and blood, reduce the growth and covering of vascular endothelial cells on the surface of the filter, and reduce the possibility that coagulation occurs to form thrombi, thereby maintaining the filter in a completely deployed state and further achieving good recovery properties of temporary filters.

However, the polymer film layer (hereinafter referred to as the film layer) is generally bound to the surface of the metal basal body (hereinafter referred to as the basal body) of the filter by means of mechanical binding with small acting force and Van der Waals force. When directly covering the surface of the filter, the film layer is unable to adhere to a metal surface in a stable and effective manner, and thus will easily fall off from the metal surface. This is particularly important for filters. Unlike other implantable medical devices (e.g., occluders or stents), when leaving the factory, filters are connected with delivery steel cables and pre-installed in guide sheaths (which are generally small 6F guide sheaths). During operation, and before implantation, a filter is required to be placed in a delivery sheath, and then implanted into a human body by means of the delivery sheath. In the process of placing the filter in the delivery sheath, the filter is compressed under stress, and intense squeezing and rubbing will occur between various parts of the filter. Moreover, during delivery in the delivery sheath (which generally has a length of about 550 mm), it is inevitable that the filter will also rub against the inner wall of the delivery sheath; if the binding force between the film layer and the basal body is insufficient, the film layer will easily fall off after this series of squeezing and rubbing, and it might even fall off from the basal body in sheets.

The surface of the metal basal body from which the film layer falls off will be in direct contact with the inner walls of a blood vessel. In such a case, endothelial cells will tend to grow and cover the metal surface, thus hampering recovery. Moreover, the fallen-off film layer may enter the lung along with blood streams to thereby block pulmonary capillaries. Alternatively, for a patient suffering from cardiac defects, the film layer may enter the patient's brain as a result of atrial septal defects to thereby block cerebral blood vessels, thus putting the patient in a life-threatening situation. Therefore, for an implantable medical device comprising a polymer film layer and a metal basal body, it is critically important to improve the binding force between the film layer and the surface of the metal basal body so as to prevent the film layer from falling off during delivery and after implantation.

SUMMARY OF THE INVENTION

Directed against the drawback existing in the prior art that a polymer film layer covering the surface of an implantable medical device and preventing endothelium growth and covering cannot be bound stably to a metal basal body, the technical problem to be solved by the present invention is to provide an implantable medical device, a preparation method thereof and an implantable medical device preform for the preparation of the above implantable medical device, wherein a polymer film layer of the implantable medical device is connected stably with a metal basal body by means of a transitional body.

The technical solution adopted by the present invention for solving its technical problem is as follows: an implantable medical device is provided, which comprises a metal basal body and a polymer film layer covering the surface of the metal basal body for preventing endothelium growth and covering, wherein the implantable medical device further comprises a transitional body located between the metal basal body and the polymer film layer, which covers at least part of the surface of the metal basal body, and the transitional body connects the polymer film layer and the metal basal body.

In the implantable medical device according to an embodiment of the present invention, the transitional body covers part of the surface of the metal basal body, and the thickness of the transitional body is 1-100 nm.

In the implantable medical device according to an embodiment of the present invention, the transitional body covers the entire surface of the metal basal body, and the thickness of the transitional body is 1-100 nm.

In the implantable medical device according to an embodiment of the present invention, the transitional body comprises at least one of amorphous carbon, titanium oxide, titanium nitride, titanium carbide and titanium carbonitride.

In the implantable medical device according to an embodiment of the present invention, the polymer film comprises at least one of polyethylene glycol-like polymers, polyethylene oxide-like polymers, polyethylene glycol-like derivatives and polyethylene oxide-like derivatives.

In the implantable medical device according to an embodiment of the present invention, the polymer film layer comprises at least one of polyethylene glycol, polyethylene glycol-like, polyethylene diether, crown ether, polyethylene diether-like, polyvinyl alcohol, polyvinyl ether, polyethylene oxide, polyethylene oxide alcohol, polyethylene oxide ether, polyethylene oxide alcohol-like and polyethylene oxide ether-like.

In the implantable medical device according to an embodiment of the present invention, the metal basal body and the transitional body are connected with each other via chemical bonding.

The present invention also provides a preparation method for an implantable medical device. The method comprises covering at least part of the surface of a metal basal body with a transitional body: covering the transitional body and the surface of the metal basal body with a polymer film layer which prevents endothelium growth and covering; wherein the transitional body connects the metal basal body and the polymer film layer.

In the preparation method for the implantable medical device according to an embodiment of the present invention, the transitional body comprises at least one of amorphous carbon, titanium oxide, titanium nitride, titanium carbide and titanium carbonitride.

In the preparation method for the implantable medical device according to an embodiment of the present invention, the surface of the metal basal body is covered with the transitional body by a vapor deposition method.

In the preparation method for the implantable medical device according to an embodiment of the present invention, the transitional body and the surface of the metal basal body is covered with the polymer film layer by a chemical vapor deposition method; the polymer film layer comprises at least one of polyethylene glycol-like polymers, polyethylene oxide-like polymers, polyethylene glycol-like derivatives and polyethylene oxide-like derivatives.

In the preparation method for the implantable medical device according to an embodiment of the present invention, the covering of the surface of the metal basal body with the transitional body and the covering of the transitional body and the surface of the metal basal body with the polymer film layer are completed in the same apparatus in situ.

In the preparation method for the implantable medical device according to an embodiment of the present invention, prior to the covering the surface of the metal basal body with the transitional body, the preparation method further comprises cleaning the metal basal body; the cleaning of the metal basal body and the covering of the surface of the metal basal body with the transitional body are completed in the same apparatus in situ.

In the preparation method for the implantabla medical device according to an embodiment of the present invention, the apparatus comprises a radio frequency or microwave power source.

The present invention further provides an implantable medical device preform comprising a metal basal body, wherein the implantable medical device preform also comprises a transitional body covering at least part of the surface of the metal basal body, and the metal basal body and the transitional body are connected with each other via chemical bonding.

In the implantable medical device preform according to an embodiment of the present invention, the transitional body covers at least part of the surface of the metal basal body, and the thickness of the transitional body is 1-100 nm.

In the implantable medical device preform according to an embodiment of the present invention, the transitional body covers the entire surface of the metal basal body, and the thickness of the transitional body is 1'-100 nm.

In the implantable medical device preform according to an embodiment of the present invention, the transitional body comprises at least one of amorphous carbon, titanium oxide, titanium nitride, titanium carbide and titanium carbonitride.

In the implantable medical device and preparation method thereof and the implantable medical device preform for the preparation of the above implantable medical device according to embodiments of the present invention, a transitional body is also provided, which connects the polymer film layer and the metal basal body. As a result, the polymer film layer will not easily fall off during the delivery process, thereby playing an effective role in preventing endothelium growth and covering in a human body.

BRIEF DESCRIPTION OF THE DRAWINGS

The present invention will be further illustrated below in conjunction with the accompanying drawings and embodiments. In the drawings.

DETAILED DESCRIPTION OF THE INVENTION

In order to have a clearer understanding of the technical features, objectives and effects of the present invention a filter is taken as an example to describe the specific implementations of the present invention in detail with reference to the accompanying drawings. Those skilled in the art should appreciate that taking the filter as an example is not intended to limit the present invention, and that all other implantable medical devices (e.g., luminal stents and occluders) fall within the scope of protection of the present invention as long as they are implemented based on the teachings of the present invention.

Figure 1:
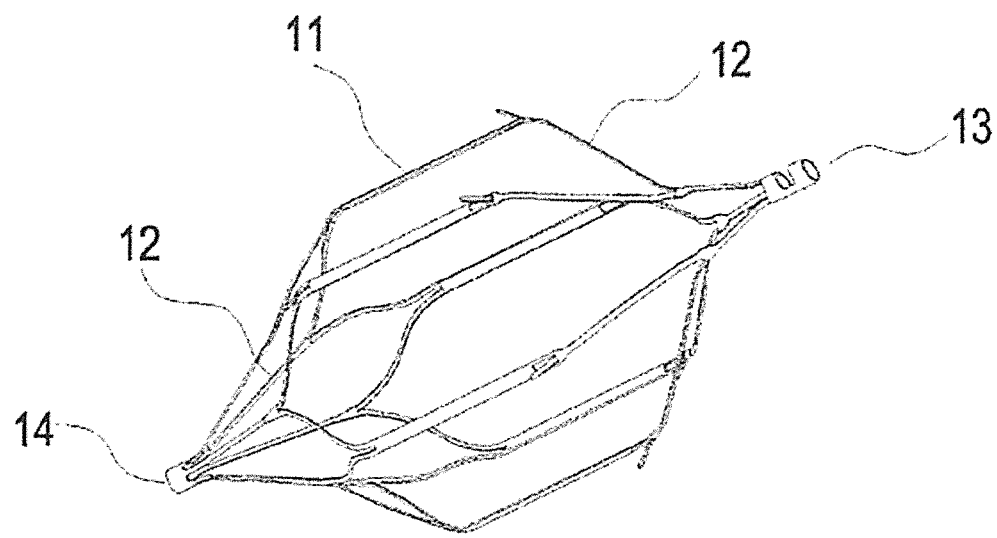
FIG. 1 is a schematic diagram illustrating the structure of an implantable medical device of an embodiment of the present invention.

As shown in FIG. 1, at least part of an implantable medical device 1 (with a filter taken as an example) according to an embodiment of the present invention needs to be in direct contact with blood vessel walls after being implanted into a human body. For example, a filter 1 in the drawing comprises a plurality of supporting bars 11 and a plurality of connecting bars 12 disposed on both sides of the supporting bars 11, wherein each of the supporting bars 11 is uniformly distributed in the circumferential direction, and wherein ends of the plurality of connecting bars 12 are connected with the supporting bars 11, while the opposite ends converge to form a Y-shaped structure and finally lead to the formation of a proximal end 13 or a distal end 14. After radial deployment, the above supporting bars 11 are in direct contact with blood vessel walls to stably dispose the filter 1 in the blood vessel through radial supporting force, thus avoiding the occurrence of displacement. Certainly, the structure shown in the figure is used merely as an illustration, and does not constitute any limitations to the present invention. The filter may also be embodied in other structures. For example, each of the supporting bars may be provided with a connecting bar on one side only, wherein ends of various connecting bars are connected with the supporting bars, while the opposite ends converge to form a distal end. Moreover, an opposite side of each of the supporting bars can be of an open structure.

Figure 2:
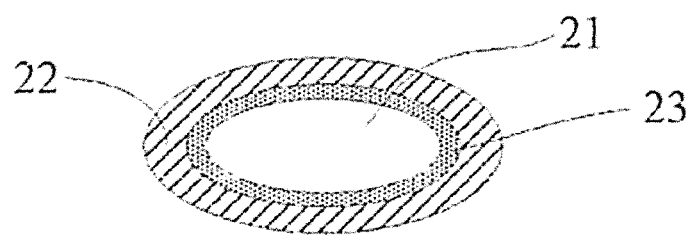
FIG. 2 is a schematic cross-sectional diagram of a part in contact with blood vessel walls as shown in FIG. 1.

Referring to FIG. 2, in the implantable medical device, the part which at least comes into contact with blood vessel walls (e.g., the supporting bars 11 in FIG. 1) comprises a metal basal body 21, a polymer film layer 22 covering the metal basal body 21 and which can preventing endothelium growth and covering, and a transitional body 23 located between the metal basal body 21 and the polymer film layer 22 and covering the surface of the metal basal body 21, wherein the transitional body 23 connects the polymer film layer 22 and the metal basal body 21. The part (e.g., the connecting bars 12 in FIG. 1) in the implantable medical device that does not come into contact with blood vessel walls may employ the same structure as the supporting bars 11. Moreover, it may also be simply the structure of the metal basal body 21 or the structure in which the polymer film layer 22 directly covers the metal basal body 21.

Under the circumstances that the structure remains unchanged, the above implantable medical device may also be characterized as follows: the implantable medical device comprises an implantable medical device preform and a polymer film layer covering this preform; the preform comprises a metal basal body and a transitional body covering the metal basal body partially or entirely, wherein the metal basal body and the transitional body are connected with each other via chemical bond.

The metal basal body (hereinafter referred to as the basal body) may be prepared by one of 316L stainless steel, nickel-titanium alloys, metallic titanium, Phynox alloys (cobalt, chromium, iron, nickel and molybdenum alloys) and tantalum alloys with good biocompatibilities, and the basal body may be prepared through the arrangement of its structure or with memory alloy materials (e.g., nickel-titanium alloys), such that the basal body has a radial compressed state and a radial deployed state. The basal body may be radially compressed and pushed into a sheath tube; then, it is delivered into a lumen via the sheath tube; after the basal body is released from the sheath tube of a delivery system, its deformation may be restored to the radial deployed state, such that the basal body is pressed to inner walls of the lumen to be secured therein. After being implanted into the lumen, the metal basal body may block and retain thrombi, thereby achieving filtering on thrombi.

Figure 3:
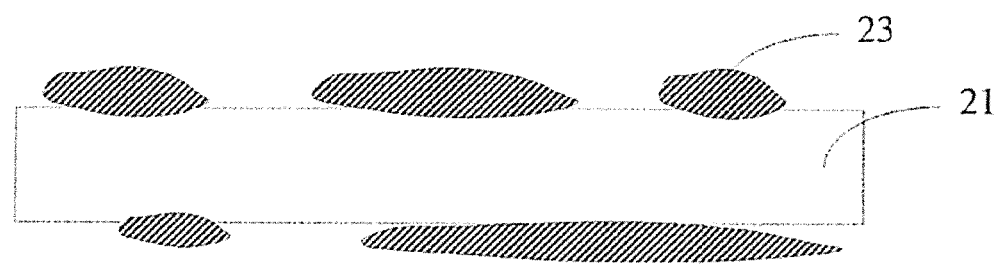
FIG. 3 is a schematic diagram illustrating a transitional body's covering part of the surface of a metal basal body in an embodiment of the present invention.
Figure 4:
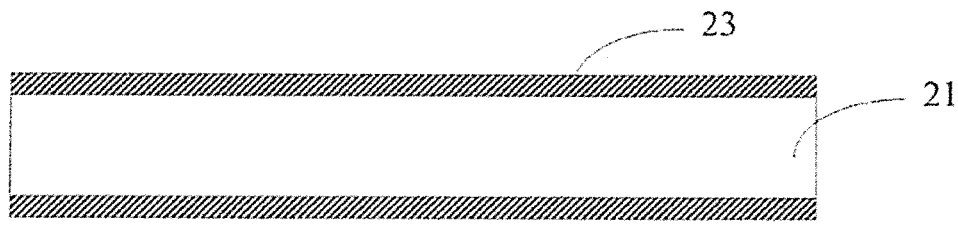
FIG. 4 is a schematic diagram illustrating the transitional body's covering the entire surface of the metal basal body in an embodiment of the present invention.

The transitional body comprises at least one of amorphous carbon, titanium oxide ($TiO_2$), titanium nitride (TiN), titanium carbide (TiC), and titanium carbonitride (TiCN). Referring to FIG. 3, the transitional body may cover part of the surface of the metal basal body. In other words, the transitional body does not form a complete integral structure; on the contrary, it exposes part of the metal basal body. Moreover, the thickness of the transitional body is 1-100 nm at a single point. Referring to FIG. 4, the transitional body may also cover, in its entirety, the entire surface of the metal basal body to form an integral film layer, and the thickness of the transitional body is 1-100 nm.

Here, the binding between the surface of the metal basal body and the transitional body comprises not only mechanical and physical binding, but also chemical binding. Specifically, metallic element Me (Me includes, but is not limited to: cobalt, chromium, iron, nickel, molybdenum, titanium, platinum and tantalum) in the metal basal body may be bound to a non-metallic element in the transitional body to form at least one of Me—C, Me—O, Me—N and Me—CN chemical bonds, wherein these chemical bonds may be ionic bonds, covalent bonds and metal bonds. With an amorphous carbon transitional body as an example, after amorphous carbon deposits and covers the surface of the metal basal body, chemical bond Me—C is formed between a carbon element and a metallic element, which takes the form of an ionic bond. Meanwhile, the concentration of carbon atoms deposited on the surface of the basal body is high. Due to the existence of concentration gradient, carbon atoms are endowed with driving force to penetrate into the metal basal body. The carbon atoms penetrating into the metal basal body will form ionic bonds with metallic elements, while the carbon atoms on the surface of the basal body will be bound to those penetrating into the inside of the basal body in the form of covalent bonds. It has been known that a chemical bond formed between atoms exists between the foregoing metallic element and the foregoing non-metallic element, and that the bonding energy is 0.5-10 eV, which is far greater than that of 0.1-0.5 eV between Van der Waals forces. Consequently, with this bonding energy, it is more difficult for the same external force to separate the transitional body from the surface of the metal basal body, and the transitional body may be bound stably to the metal basal body.

On the other hand, the transitional body covering the metal basal body may also effectively prevent the release of metal ions in the body. This is particularly important for the nickel-titanium alloy filter. This transitional body isolates the basal body to thereby effectively prevent the release of harmful nickel ions in the nickel-titanium alloy into surrounding tissues and blood, thus further enhancing the biocompatibility of the filter and reducing the occurrence of inflammations.

The polymer film layer generally has a thickness of less than 3 μm, which may be at least one of polyethylene glycol-like polymers, polyethylene oxide-like polymers, polyethylene glycol-like derivatives and polyethylene oxide-like derivatives. Specifically, the polymer film layer may be at least one of polyethylene glycol (PEG), polyethylene glycol-like (PEG-like), polyethylene diether, crown ether (e.g., 12-crown ether-4), polyethylene diether-like, polyvinyl alcohol, polyvinyl ether, polyethylene oxide (PEO), polyethylene oxide alcohol, polyethylene oxide ether, polyethylene oxide alcohol-like and polyethylene oxide ether-like. The polymer film layer covering the outermost surface of the medical device may significantly improve the hydrophilicity of the surface of the device, reduce roughness, and greatly reduce the absorption of bacteria and proteins on the material's surface, prevent endothelium growth and covering. Meanwhile, it can also enhance anticoagulant properties of the material.

Figure 5:
FIG. 5 is a schematic cross-sectional diagram of a filter in an embodiment of the present invention.

As shown in FIG. 5, the case in which a transitional body 23 covers the entire surface of a metal basal body 21 is taken as an example. In such case, a filter comprises the metal basal body 21, the transitional body 23 covering the entire metal basal body 21, and a outermost polymer film layer 22 covering the metal basal body 21 and the transitional body 23. At least one of a C—C bond, C—O bond, C—N bond and other covalent bond may be formed between the polymer film layer 22 and the transitional body 23, such that the polymer film layer 22 and the transitional body 23 are connected with each other via a covalent bond. Similarly, the bonding energy of this covalent bond is 0.5-10 eV, which is far greater than that of 0.1-0.5 eV between Van der Waals forces. Consequently, with this bonding energy, it is difficult for the same external force to separate the transitional body 23 from the polymer film layer 22, and the transitional body 23 may be bonded stably to the polymer film layer 22. As has been mentioned above, the transitional body 23 may be bonded stably to the metal basal body 21 via a chemical bond. Therefore, in combination with the transitional body 23 being bonded to the polymer film layer 22 stably via a covalent bond, the transitional body 23 may be utilized to enhance the binding force between the polymer film layer 22 and the surface of the metal basal body 21, thereby achieving a stable and effective attachment of the polymer film layer 22 to the metal basal body 21.

After the filter that has been prepared through the above preparation method of the present invention is implanted into a lumen, as the polymer film layer 22 may be connected stably and effectively with the metal basal body 21 through the transitional body 23, the possibility that the polymer film layer 22 falls off when the filter enters and exits a sheath tube, and after it is implanted into the lumen, is extremely low. Consequently, the polymer film layer 22 may exert its function effectively and improve the resistance properties of the filter against endothelium growth and covering. On the other hand, after the filter is implanted into the lumen, even if the hydrophilic polymer film layer 22 hydrolyzes over time, the transitional body 23 connected stably on the surface of the metal basal body 21 may also effectively prevent the release of metallic elements in the lumen, thus reducing the damage caused by the filter to a human body.

Figure 6:
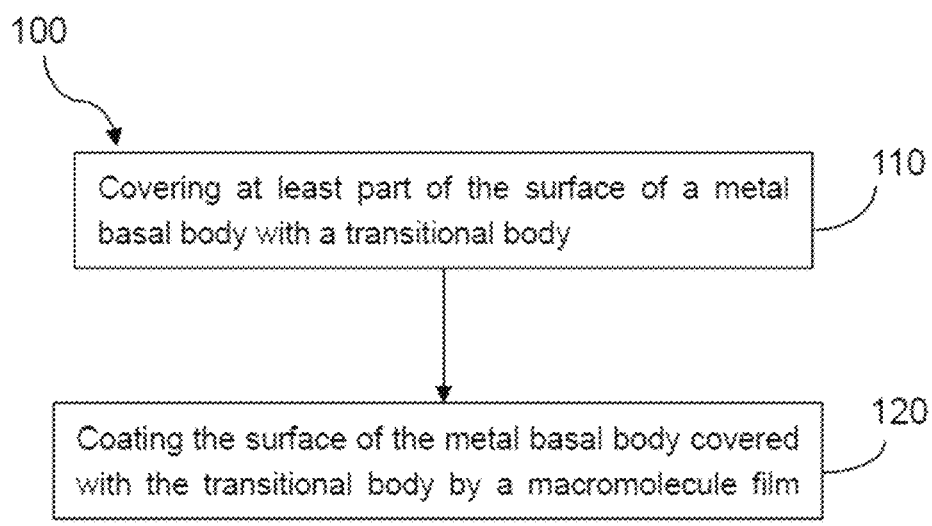
FIG. 6 is a flow diagram illustrating a preparation method of the implantable medical device in accordance with an embodiment of the present invention.

FIG. 6 is a flow diagram illustrating a preparation method 100 for an implantable medical device (with a filter taken as an example) in accordance with an embodiment of the present invention. As shown in FIG. 6, in step 110, the surface of a metal basal body is first covered with a transitional body to form an implantable medical device preform.

The transitional body comprises at least one of amorphous carbon, titanium oxide ($TiO_2$), titanium nitride (TiN), titanium carbide (TiC) and titanium carbonitride (TiCN), and a vapor deposition technique may be used to cover the surface of the basal body with the transitional body comprising at least one of the above amorphous carbon, titanium oxide ($TiO_2$), titanium nitride (TiN), titanium carbide (TiC) and titanium carbonitride (TiCN). The vapor deposition technique is one in which a physical or chemical process occurring in a vapor phase is utilized to form a functional or decorative metallic, non-metallic or compound coating on the surface of a workpiece. The vapor deposition technique may be classified into chemical vapor deposition (CVD) and physical vapor deposition (PVD) according to the mechanism of film formation.

In the vapor deposition technique, the deposition power and time may be regulated to control the amount of deposition of the transitional body on the surface of the metal basal body. As shown in FIG. 3, the transitional body 23 is controlled to uniformly cover part of the surface of the metal basal body 21, and the thickness of the transitional body 23 is 1-100 nm at various points. As the polymer film layer 22 is formed by polymers comprising chain structures, even if the transitional body 23 only covers part of the surface in a scattering manner, the transitional body 23 can still be connected effectively to the polymer film layer 22 and the metal basal body 21 through the intertwining and constraining among the chain structures, thereby preventing the polymer film layer 22 from falling off from the metal basal body 21. Generally, the higher the coverage rate of the transitional body 23 on the metal basal body 21, the better the binding effect between the basal body 21 and the polymer film layer 22. As shown in FIG. 4, the transitional body 23 may also be controlled to cover the entire surface of the metal basal body 21 to form an integral film layer. The thickness of this transitional body film layer is 1-100 nm, which enables the transitional body 23 to effectively connect the polymer film layer 22 and the metal basal body 21.

In step 120, a polymer film layer 22 is coated on the surface of the metal basal body 21 covered with a transitional body 23 in step 110, such that the transitional body 23 connects the metal basal body 21 and the polymer film layer 22.

A chemical vapor deposition method (e.g., radio frequency plasma enhanced chemical vapor deposition (RF-PECVD) and microwave electron cyclotron resonance plasma assisted chemical vapor deposition (ECR-CVD)) may be used to cover the transitional body and the surface of the metal basal body with the polymer film layer. The prepared polymer film comprises at least one of polyethylene glycol-like polymers, polyethylene oxide-like polymers, polyethylene glycol-like derivatives and polyethylene oxide-like derivatives; specifically, the polymer film may be at least one of polyethylene glycol, polyethylene glycol-like, polyethylene diether, crown ether, polyethylene diether-like, polyvinyl alcohol, polyvinyl ether, polyethylene oxide, polyethylene oxide alcohol, polyethylene oxide ether, polyethylene oxide-like alcohol and polyethylene oxide ether-like.

For example, in the process of preparing the polymer film layer through the chemical vapor deposition method, monomer molecules may be ionized, and react and polymerize to form a polymer film layer coated metal basal body. Here, monomer molecules comprise at least one of ethylene glycol, diethylene glycol, ethylene glycol dimethyl ether, diethylene glycol dimethyl ether, triethylene glycol dimethyl ether and tetraethylene glycol dimethyl ether. Furthermore, as steps 110 and 120 may be implemented with the same method (e.g., the chemical vapor deposition method), steps 110 and 120 may be completed in the same equipment in situ, and the equipment may comprise a radio frequency power source and a microwave power source. For example, with an amorphous carbon transitional body as an example, in step 110, hydrocarbon gas may be used as a gas source to complete the deposition of the amorphous carbon transitional body; after that, in step 120, triethylene glycol dimethyl ether is used to replace the hydrocarbon gas, and serves as the gas source to complete the coating of a polymer film layer in the same reaction chamber, wherein the metal basal body requires no displacement during these two steps. As the above two steps may be completed in the same equipment in situ, the metal basal body requires no displacement in the whole process, and thus will not lead to secondary pollution. Moreover, working procedures are simple, thus improving production efficiency and reducing equipment costs.

In order to further improve the properties of the filter, the metal basal body may be cleaned prior to step 110. For example, the metal basal body may be placed in the same equipment in which steps 110 and 120 are implemented, and receives plasma cleaning under vacuum conditions. In this manner, even if cleaning is conducted for the metal basal body, it may also be completed in the same equipment in situ. In addition, the metal basal body may be ultrasonically cleaned in advance.

EMBODIMENT 1

In this embodiment, a hydrocarbon gas is taken as a carbon source, and an amorphous carbon transitional body is deposited and coated on the surface of a metal basal body by a chemical vapor deposition method. For example, the metal basal body may be placed in a reaction chamber, and the hydrocarbon gas is taken as the carbon source to generate carbon and/or hydrocarbon ions; then, these ions are directed towards the metal basal body by magnetic fields or bias voltages, and deposited on the surface of the metal basal body to form a hydrogen-containing or hydrogen-free amorphous carbon transitional body. The chemical vapor deposition method comprises radio frequency plasma enhanced chemical vapor deposition (RF-PECVD) and microwave electron cyclotron resonance plasma assisted chemical vapor deposition (ECR-CVD), and the hydrocarbon gas adopted as the carbon source comprises at least one of methane, ethane, acetylene, butane and benzene. During deposition, hydrogen may be pumped into the chamber to mix with the above hydrocarbon gas to change into a reaction gas, thus increasing the proportion of C—H bonds. Argon may also be used as an auxiliary gas to mix with the hydrocarbon gas or with the hydrocarbon gas and hydrogen, thereby contributing to the generation of plasma. This amorphous carbon has no crystal structure. It is the allotrope of short-range ordered carbon and long-range disordered carbon, comprising diamond-like carbon, vitreous carbon and amorphous carbon.

Specifically, prior to step 110, plasma cleaning is conducted for the metal basal body used to prepare the filter. Specifically, the filter is placed on a sample holder in a vacuum chamber, and the chamber is vacuumed to be below 8.0 Pa; argon with a flow of 20-200 sccm is pumped into the chamber to maintain the pressure in the vacuum chamber to be below 10.0 Pa; a radio frequency or microwave power source is turned on to ionize the gas and apply a bias voltage of 10-500 V to the metal basal body; under such conditions, plasma cleaning is conducted for the surface of the metal basal body for 5-60 minutes.

In step 110, the chemical vapor deposition method is used to deposit the amorphous carbon transitional body on the surface of the metal basal body. Specifically, the hydrocarbon gas methane is pumped into the chamber at a flow of 10-50 sccm. In order to increase the amount of plasma, the auxiliary gas argon is mixed while methane is pumped into the chamber, wherein the flow of argon is 50-200 sccm. Meanwhile, the vacuum pressure in the reaction chamber is maintained to be below 10.0 Pa. The radio frequency power is regulated to be 200 W-1000 W and the bias voltage to be 10 V-500 V, and deposition is conducted for 1-60 minutes under the above conditions; then, the reaction gas is cut off, and the radio frequency power source and the bias voltage are turned off. At this point, the amorphous carbon transitional body covers the entire surface of the metal basal body, and its thickness is 1-100 nm.

In step 120, the outermost layer of the surface of the metal basal body is coated with a polymer film layer. A radio frequency plasma enhanced chemical vapor deposition (RF-PECVD) method is adopted in this embodiment, and the polymer film layer is a PEG-like film layer. Specifically, argon is pumped into the chamber at a flow of 10-100 sccm; the atmosphere pressure in the reaction chamber is controlled to be 2-7 Pa, which is 1-2 Pa lower than the pressure set by reactive deposition; the needle valve of the heated (the heating temperature is set to be 80-150 degrees Celsius) triethylene glycol dimethyl ether reaction gas bottle is opened to regulate the pressure of the vacuum chamber to be the pressure set by deposition, and the pressure set by reactive deposition is 3-9 Pa; the power of the radio frequency power source is regulated to be 20 W-200 W, and the bias voltage to be 10 V-200 V, and deposition is conducted for 10-60 minutes under the above conditions. After deposition is completed, all the reaction gases are cut off, the radio frequency power source and bias voltage are turned off, the vacuum pump is shut off, and the finished filter product is taken out.

The schematic cross-sectional diagram of the filter prepared in Embodiment 1 is similar to that shown in FIG. 5. The surface of the metal basal body 21 of this filter is coated with a layer of amorphous carbon transitional body 23, and the transitional body 23 serves as a film layer and entirely covers the metal basal body 21; a PEG-like film layer 22 is coated on the surface of the transitional body 23 to prevent endothelium growth and covering.

EMBODIMENT 2

This embodiment is different from Embodiment 1 in the following aspect: in step 110, graphite is taken as a carbon source, and an amorphous carbon transitional body is deposited and coated on the surface of a metal basal body by a physical vapor deposition method. For example, the metal basal body may be placed in a reaction chamber, and with graphite taken as the carbon source, such methods as vacuum evaporation plating, arc ion plating or sputter coating are used to deposit amorphous carbon on the surface of the metal basal body. This amorphous carbon has no crystal structure. It is the allotrope of short-range ordered carbon and long-range disordered carbon, comprising diamond-like carbon, vitreous carbon and amorphous carbon; moreover, adopting graphite as the carbon source will generate hydrogen-free amorphous carbon.

EMBODIMENT 3

This embodiment is different from Embodiment 1 in the following aspect: in step 110, an evaporation coating process is used to cover the surface of a metal basal body with a transitional body. Specifically, under vacuum conditions, a plating material is converted into a vapor phase using the method of heating evaporation, wherein the plating material comprises at least one of amorphous carbon, titanium oxide, titanium nitride, titanium carbide and titanium carbonitride; the method of heating evaporation comprises resistance heating, electron beam heating, high frequency induction heating, etc. Then, the plating material after evaporation is condensed on the surface of the basal body to achieve the transitional body's covering the basal body. This method has the following advantages: the apparatus and processes are simple, plasma is not generated in the evaporation process, and the temperature of the basal body is low.

EMBODIMENT 4

This embodiment is different from Embodiment 1 in the following aspect: in step 110, a reactive deposition method is used to cover the surface of a metal basal body with a transitional body. Specifically, in a vacuum chamber, metallic titanium is taken as a target material. An inert gas (e.g., argon) is pumped into the vacuum chamber where it is ionized under the action of electrical fields such as direct current, intermediate frequency, radio frequency or cathodic multiple arcs and accelerates to fly to the metallic target, such that titanium atoms on the target acquire sufficient energy and are thus sputtered to form a vapor phase. A reaction gas (e.g., at least one of $O_2$, $N_2$, $CO_2$ and $CH_4$) is pumped into the vacuum reaction chamber while sputter coating is conducted, thereby obtaining a compound (e.g., at least one of $TiO_2$, TIN, TiC and TiCN) of the target material with the reaction gas. Here, if two or more reaction gases (e.g., a mixed gas of $N_2$ and $CO_2$, a mixed gas of $N_2$ and $CH_4$, or a mixed gas of $N_2$, $CO_2$ and $CH_4$) are pumped into the vacuum chamber, TiCN may be generated. Accordingly, the surface of the basal body may be covered with at least one of titanium oxide, titanium nitride, titanium carbide and titanium carbonitride as the transitional body.

The filter prepared in the above Embodiment 1 is labeled as a sample 1, and another filter sample 2 is prepared to be compared with the sample 1, The sample 2 is prepared using the same metal basal body, cleaning steps and step 120 as those in Embodiment 1, but step 110 is omitted. Therefore, the sample 2 only comprises a metal basal body and a PEG-like film layer coated on the metal basal body. In-vitro simulation experiments (namely the simulation of the process of pushing a filter into a delivery sheath tube, and releasing and recovering it from the sheath tube) are conducted for the samples 1 and 2 under identical conditions.

Specifically, first of all, a filter (the sample 1 or the sample 2), a guide sheath, a delivery sheath and a delivery steel cable are soaked in water having a temperature of 37 degrees Celsius, and a simulation experiment is completed in water having a temperature equal to the normal temperature of a human body; the delivery steel cable is made to pass through a 6F guide sheath having a length of 85 mm; then, the filter is secured on the delivery steel cable using a connecting nut on the filter; the delivery steel cable is removed, and the filter is placed in the 6F guide sheath; the guide sheath is inserted into a 6F delivery sheath having a length of 550 mm, and the delivery steel cable is propelled to push the filter into the delivery sheath; the steel cable is propelled continuously until the filter is pushed to another end of the delivery sheath; the filter is grasped manually, and it is rotated counterclockwise to be removed from the delivery steel cable; water on the filter is sucked dry by filter paper, and the filter is placed under an optical microscope to observe the falling-off situation of the polymer film layer.

Figure 7:
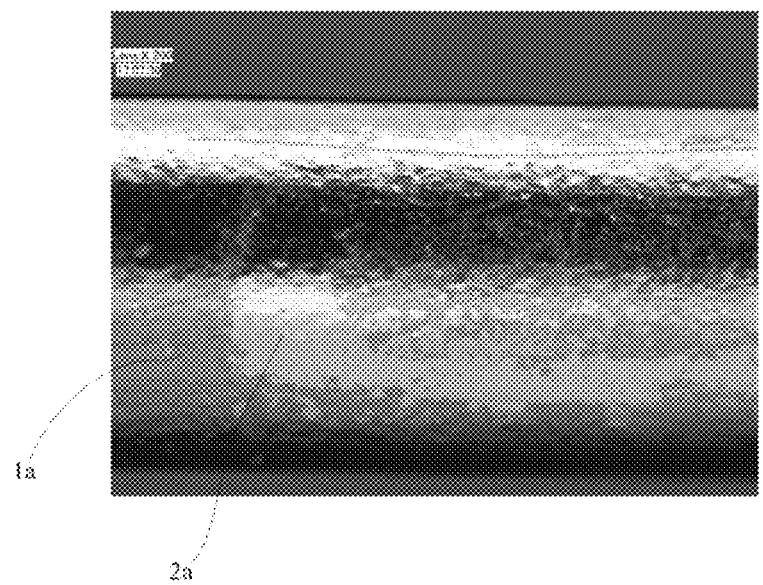
FIG. 7 illustrates an optical microscopic photograph of a sample 2 after an in-vitro simulation experiment in an embodiment of the present invention.
Figure 8:
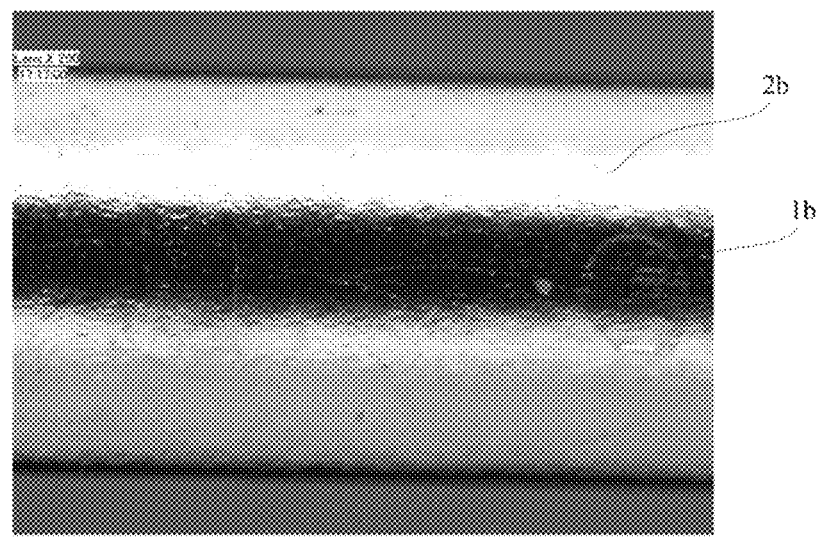
FIG. 8 illustrates an optical microscopic photograph of a sample 1 after an in-vitro simulation experiment in an embodiment of the present invention.

FIG. 7 illustrates an optical microscopic photograph of the sample 2 after the in-vitro simulation experiment, and the magnification is 200 times. As can be seen from FIG. 7, in the above in-vitro simulation experiment, after the surface of the filter comes into direct contact with and rubs against the inner walls of sheath tubes, a PEG-like film layer 1*a* falls off in sheets (see the region designated at 2*a*). FIG. 8 illustrates an optical microscopic photograph of the sample 1 after the in-vitro simulation experiment, and the magnification is likewise 200 times. As can be seen from FIG. 8, in the above in-vitro simulation experiment, after the surface of the filter comes into direct contact with and rubs against the inner walls of sheath tubes, a PEG-like film layer 1*b* shows no falling-off phenomenon, and a white bright region 2*b* in FIG. 8 is caused by light reflection. As can be known from the comparison between FIG. 7 and FIG. 8, for the sample 2, as the binding force between the PEG-like film layer (designated at 1*a*) directly deposited on the surface of the metal basal body and the metal basal body is smaller, the PEG-like film layer will easily fall off from the surface of the metal basal body; for the sample 1, as the surface of the metal basal body and the PEG-like film layer 1*b* are bound stably by means of the amorphous carbon transitional body, the PEG-like film layer will not easily fall off.

In order to verify the inhibition effects of the filter prepared through the preparation method of the present invention on endothelium growth and covering, the above samples 1 and 2 were implanted into the inferior vena cava blood vessel of the same ram together with a sample 3, wherein the sample 3 only comprised the same metal basal body as the samples 1 and 2, without the amorphous carbon transitional body and the polymer film layer. Four weeks after implantation, the endothelium growth and covering situations of the above three samples in the inferior vena cava blood vessel were observed.

As sample 3 only comprised the metal basal body, endothelium grew on the entire surface of the filter after implantation. In the case that the part of the metal basal body that is in contact with blood vessel walls is completely covered, successful removal of the filter using the vascular recovering method will be impossible, and even if the filter is forcibly removed, blood vessel walls will be injured.

Endothelium growth and covering was found on part of the surface of the sample 2. This was because the surface of its metal basal body was coated with the PEG-like film layer and thus could inhibit endothelium growth and covering. However, as the PEG-like film layer was directly coated on the metal basal body, the binding force between them was smaller. In such case, during the rubbing of the filter against the delivery sheath tubes, the PEG-like film layer easily fell off, and after the film layer fell off, the exposed metal basal body was ineffective in preventing endothelium growth and covering. Consequently, this exposed part was subject to severe endothelium growth and covering. If this filter is recovered intravascularly, the endangium will be severely injured when the part on which endothelium grows and covers is torn, and it might even be impossible to successfully remove the filter.

There was almost no endothelium growth and covering on the surface of the sample 1. This was because the PEG-like film layer was bound stably to the metal basal body through the deposited amorphous carbon transitional layer. Consequently, the falling-off of the PEG-like film layer was substantially avoided during entry into and withdrawal from sheath tubes and after implantation, thereby effectively inhibiting endothelium growth and covering. This filter can still be removed successfully through the intravascular recovering method even after being implanted into a human body for more than four weeks, without injuring endangium.

From the above, it can be seen that four weeks after implantation, the existing temporary filters (e.g., the above samples 2 and 3) are subject to severe endothelium growth and covering. In order to recover filters from blood vessels in a safe manner, the time window for safe removal of the existing filters is generally about 14 days. For the filter (e.g., the sample 1) prepared through the preparation method of the present invention, as the polymer film layer may be stably coated on the metal basal body and can effectively prevent endothelium growth and covering, the time window for safe removal of the filter may be extended to at least one month. The extension of the time window for safe removal may prolong the time for clinical observation and expand the range of the target population. For example, the filter according to the embodiments of the present invention may be applied to patients requiring long-term implantation of filters, thus avoiding the repeated implantation of traditional temporary filters or the implantation of permanent filters into such patients.

From the above it can be seen that in the preparation method of the implantable device of the present invention, the surface of a metal basal body is initially covered with a transitional body, and then a polymer film layer for preventing endothelium growth and covering is coated on the transitional body and the metal basal body. In the implantable device prepared therefrom, the non-metallic element in the transitional body forms a chemical bond with the metallic element in the metal basal body, and the bonding energy is far greater than that between molecules. Consequently, the transitional body may be bound stably to the metal basal body; on the other hand, the polymer film layer is finally coated on the outermost layer of the metal basal body. This polymer film layer forms a chemical bond with the non-metallic element in the transitional body, and the bonding energy is also large. Therefore, the transitional body may be bound stably to the polymer film layer. As such, with the transitional body serving as the medium, the polymer film layer may be connected stably to the metal basal body, such that while the prepared filter is inserted into and withdrawn from sheaths and being implanted, the polymer film layer on its surface will not easily fall off.

The above specific embodiments are provided only as illustrations and do not constitute any limitations to the present invention. Those skilled in the art may employ any suitable methods to prepare a filter on the basis of the teachings in the present invention. The prepared filter has the following features: the polymer film layer will not easily fall off, resistance properties against endothelium growth and covering are good, and the time window for safe removal is long.

The invention claimed is:

1. A method of preparing an implantable medical device, comprising:
   providing a metal basal body in a chamber, the metal basal body having a metallic element that is selected from a group consisting of cobalt, chromium, iron, nickel, molybdenum, titanium, platinum and tantalum;
   depositing an amorphous carbon transitional body on the surface of a metal basal body via a chemical vapor deposition method where a hydrocarbon gas is pumped into the chamber at a flow of 10-50 sccm, while the vacuum pressure in the chamber is maintained to be below 10.0 Pa, the radio frequency power is regulated to be 200 W-1000 W, and the bias voltage to be 10 V-500 V, and wherein the deposition is conducted for 1-60 minutes, and wherein the amorphous carbon transitional body covers part of the surface of the metal basal body in a manner that exposes part of the metal basal body, and has a thickness of 1-100 nm;
   covering the transitional body and the surface of the metal basal body with a polymer film layer via a radio frequency plasma enhanced chemical vapor deposition (RF-PECVD) method by pumping argon into the chamber at a flow of 10-100 sccm while the atmosphere pressure in the chamber is controlled to be 2-7 Pa, the power of the radio frequency power source is regulated to be 20 W-200 W, and the bias voltage to be 10 V-200 V, and the deposition is conducted for 10-60 minutes;
   wherein the polymer film layer is selected from a group consisting of polyethylene glycol, polyethylene diether, crown ether, polyvinyl alcohol, polyvinyl ether, polyethylene oxide, polyethylene oxide alcohol, polyethylene oxide ether; and
   wherein the polymer film layer prevents endothelium growth and covering, and the transitional body connects the metal basal body and the polymer film layer.

2. The method of claim 1, further including the step of conducting plasma cleaning for the surface of the metal basal body for 5-60 minutes, which is done before the depositing step.

3. The method of claim 2, wherein the step of plasma cleaning includes:
   vacuuming the chamber to be below 8.0 Pa;
   pumping argon into the chamber with a flow of 20-200 sccm to maintain the pressure in the vacuum chamber to be below 10.0 Pa; and
   ionizing the argon by turning on a radio frequency or microwave power source to apply a bias voltage of 10-500 V to the metal basal body.

4. The method of claim 1, wherein the hydrocarbon gas is methane.

5. The method of claim 4, wherein during the depositing step, increasing the amount of plasma by mixing an auxiliary argon gas while methane is pumped into the chamber, wherein the flow of argon is 50-200 sccm.

6. The method of claim 1, wherein all the steps are completed in the same apparatus in situ.

7. A method of preparing an implantable medical device, comprising:
   providing a metal basal body in a chamber, the metal basal body having a metallic element that is selected from a group consisting of cobalt, chromium, iron, nickel, molybdenum, titanium, platinum and tantalum;
   conducting plasma cleaning for the metal basal body for 5-60 minutes;
   depositing an amorphous carbon transitional body on the surface of a metal basal body via a chemical vapor deposition method where a methane gas is pumped into the chamber at a flow of 10-50 sccm, while the vacuum pressure in the chamber is maintained to be below 10.0 Pa, the radio frequency power is regulated to be 200 W-1000 W, and the bias voltage to be 10 V-500 V, and wherein the deposition is conducted for 1-60 minutes, and wherein the amorphous carbon transitional body covers part of the surface of the metal basal body in a manner that exposes part of the metal basal body, and has a thickness of 1-100 nm;
   wherein during the depositing step, increasing the amount of plasma by mixing an auxiliary argon gas while methane is pumped into the chamber, wherein the flow of argon is 50-200 sccm;
   covering the transitional body and the surface of the metal basal body with a polymer film layer via a radio frequency plasma enhanced chemical vapor deposition (RF-PECVD) method by pumping argon into the chamber at a flow of 10-100 sccm while the atmosphere pressure in the chamber is controlled to be 2-7 Pa, the power of the radio frequency power source is regulated to be 20 W-200 W, and the bias voltage to be 10 V-200 V, and the deposition is conducted for 10-60 minutes;
   wherein the polymer film layer is selected from a group consisting of polyethylene glycol, polyethylene diether, crown ether, polyvinyl alcohol, polyvinyl ether, polyethylene oxide, polyethylene oxide alcohol, polyethylene oxide ether; and
   wherein the polymer film layer prevents endothelium growth and covering, and the transitional body connects the metal basal body and the polymer film layer.

8. The method of claim 7, wherein all the steps are completed in the same apparatus in situ.

9. The method of claim 7, wherein the step of plasma cleaning includes:
   vacuuming the chamber to be below 8.0 Pa;
   pumping argon into the chamber with a flow of 20-200 sccm to maintain the pressure in the vacuum chamber to be below 10.0 Pa; and
   ionizing the argon by turning on a radio frequency or microwave power source to apply a bias voltage of 10-500 V to the metal basal body.

* * * * *